(12) United States Patent
Glor et al.

(10) Patent No.: US 8,170,327 B2
(45) Date of Patent: May 1, 2012

(54) METHOD FOR (SEMI-) AUTOMATIC DENTAL IMPLANT PLANNING

(75) Inventors: Fadi Glor, Leuven (BE); Luc Vrielinck, Genk (BE)

(73) Assignee: Materialise Dental N.V., Heverlee (BE)

( * ) Notice: Subject to any disclaimer, the term of this patent is extended or adjusted under 35 U.S.C. 154(b) by 1034 days.

(21) Appl. No.: 11/988,725

(22) PCT Filed: Jul. 17, 2006

(86) PCT No.: PCT/EP2006/007008
§ 371 (c)(1),
(2), (4) Date: May 2, 2008

(87) PCT Pub. No.: WO2007/009719
PCT Pub. Date: Jan. 25, 2007

(65) Prior Publication Data
US 2009/0162813 A1 Jun. 25, 2009

(30) Foreign Application Priority Data
Jul. 15, 2005 (GB) .................................. 0514554.5

(51) Int. Cl.
*G06K 9/00* (2006.01)
(52) U.S. Cl. ....................................................... 382/154
(58) Field of Classification Search .................. 382/154, 382/100, 128, 132, 162, 167, 173, 228, 276, 382/308, 312, 315, 325; 345/419, 427; 356/12
See application file for complete search history.

(56) References Cited

U.S. PATENT DOCUMENTS

| | | | |
|---|---|---|---|
| 6,319,006 B1 | 11/2001 | Scherer et al. | |
| 6,648,640 B2 | 11/2003 | Rubbert et al. | |

FOREIGN PATENT DOCUMENTS

| | | |
|---|---|---|
| DE | 199 52 962 A1 | 5/2001 |
| DE | 19952962 A1 | 5/2001 |
| EP | 0 868 891 A1 | 10/1998 |
| JP | 09206320 A | 8/1997 |
| JP | 2003245289 A | 9/2003 |
| JP | 2005310749 A | 11/2005 |
| WO | 00/32258 | 6/2000 |
| WO | 03037189 A1 | 5/2003 |

OTHER PUBLICATIONS

Examination Report of Australian Patent Office (IP Australia) regarding Australian Patent Application No. 2006271950, Feb. 1, 2011.
Lewis S. Benjamin, "The Evolution of Multiplanar Diagnostic Imaging: Predictable Transfer of Preoperative Analysis to the Surgical Site", *J. Oral Implantol*, 2002; 28(3); pp. 135-144.

(Continued)

*Primary Examiner* — Brian Q Le
*Assistant Examiner* — Edward Park
(74) *Attorney, Agent, or Firm* — Bacon & Thomas, PLLC

(57) ABSTRACT

A method and system for (semi-) automatic dental implant planning (A) is described including (a) means for creating 3D models of a tooth setup (b) and/or means for creating 3D models of parts of the jaw, (c) means for detecting zones in the jaw where implants can (or optionally cannot be placed), (d) means for detecting restorative elements in the tooth setup, (e) means for determining candidate implant dimensions, positions, orientations and configurations, (f) means for obtaining implant plans, (g) means for comparing implant plans to each other or to given criteria, (h) means for selecting or improving an implant plan.

15 Claims, 11 Drawing Sheets

OTHER PUBLICATIONS

Scott D. Ganz, "The Triangle of Bone—A Formula for Successful Implant Placement and Restoration", *The Implant Society*, 1995, vol. 5, No. 5, pp. 2-6.

S. Mohandas and M. Henderson, "Pursuing Mechanical Part Feature Recognition Through the Isolation of 3D Features in Organic Shapes", Proceedings of ASME 2002—IMECE2002-DE-34419, International Mechanical Engineering Conference and Expo, Nov. 12-22, New Orleans, LA.

Official Action of Japanese Patent Office related to JP 2008-520811, Aug. 23, 2011.

Examination Report of China (PRC) I.P. Office regarding Chinese Patent Application No. 200680032233.3, Nov. 13, 2009.

Communication of Russian Patent Office regarding Russian Patent Application No. 2008105760/14 (006243), Jun. 2, 2010.

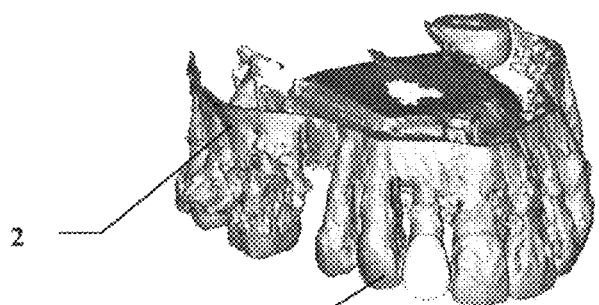
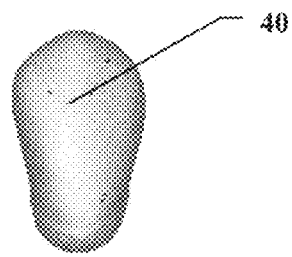
Figure 26                     Figure 27
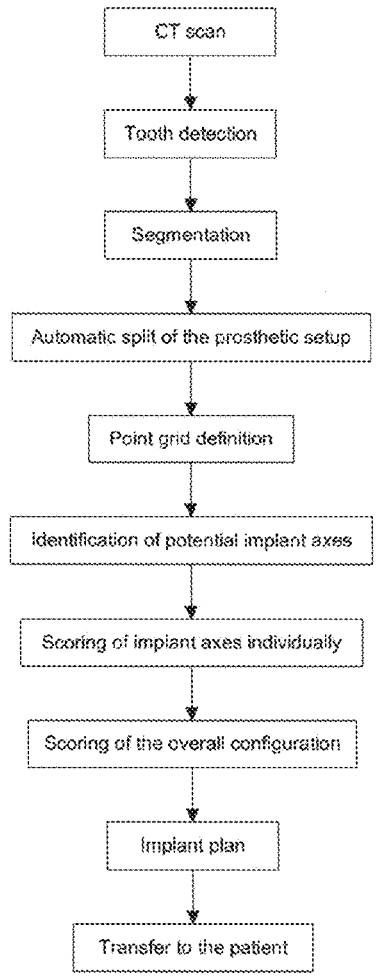
Fig. 28

METHOD FOR (SEMI-) AUTOMATIC DENTAL IMPLANT PLANNING

FIELD OF THE INVENTION

The present invention relates to methods and apparatus for (semi-) automatic dental implant planning, e.g. based on biomechanical, aesthetic and/or functional considerations as well as to computer methods, computer systems and software for implementing the methods.

TECHNICAL BACKGROUND

A dental implant is an artificial tooth root that periodontists place into the jaw to hold a replacement tooth or to support a replacement prosthesis. Treatment with dental implants is widely accepted and holds a number of advantages over other techniques such as removable partial dentures, bridges or loose prostheses. Dental implants allow reconstruction of the dentition without the need to sacrifice healthy neighbouring teeth. The loads transferred via the implants stimulate the bone, preventing bone resorption and limiting recession of the gums around the replaced tooth elements and resulting in a more aesthetic reconstruction. Treatment with implants also provides a more comfortable and stable solution than conventional dentures, guaranteeing more natural biting and chewing capacity.

Surgical planning for dental implant placement traditionally uses one or more medical imaging modalities such as an orthopantogram (i.e. an x-ray technique for imaging the bones of the jaws and the teeth) or computerized tomography (CT) scan to verify the quantity and quality of the bone. In fact, the American Association of Oral and Maxillofacial Radiologists (AAOMR) recommends that some form of cross-sectional imaging be used for implant treatment. According to the classic way of working, the final decision about the implant positions however is taken during surgery when opening of the surrounding soft tissue has exposed the bone. After an osseointegration period of 3 to 6 months secondary, mainly angular corrections are made to the direction of the implants to optimize the aesthetics of the reconstruction. Still, the design of the final implant-supported prosthesis is dictated to a large extent by the original implant positions, which may be suboptimal from an aesthetical, functional and biomechanical point of view.

The classic solution is no longer valid when evolving towards immediate loading of the implant. Immediate loading of the implants requires a flawless planning and precise surgical transfer. This planning preferably, besides being biomechanically sound, already takes into account aesthetic and/ or functional considerations, which using traditional implantlogy methods were only of importance during the actual prosthetic phase of the implant treatment.

Over the last few years several tools have been made available commercially to provide periodontists with a means to evaluate the bone of the patient in a number of differently oriented slices of a volumetric scan, such as a CT scan or other volumetric scans such as MRI and to graphically superimpose on the images representations of commercial implants of varying length, diameter and brand (see SimPlant™ provided by Materialise, Leuven, Belgium). Citing Benjamin, "Multiplanar reformatted CT, has become the most comprehensive and accurate aid for implant treatment planning" (see Benjamin L S, The evolution of multiplanar diagnostic imaging: predictable transfer of preoperative analysis to the surgical site. J Oral Implantol. 2002; 28(3): 135-44).

According to the current state of the art, treatment of a patient with dental implants consists of a number of steps. Before treatment, articulated stone models are firstly used to assess vertical dimension. Afterwards a diagnostic wax-up is created to represent the desired prosthetic end result (see FIG. 1). The wax-up is optimized to achieve proper occlusion, morphology, aesthetics and phonetics. In a next step a scanning template or scan prosthesis is manufactured (see FIG. 2). This is an exact replica of the wax-up made in a radiopaque material, typically a cold-polymerizing resin mixed with a certain percentage of barium sulfate. The level of opacity of the scan prosthesis may vary for its constituent parts: for instance the teeth may have a higher opacity than the base plate. If desired, some parts can be made radio-transparent. When the patient is scanned with the scan prosthesis in the mouth, the radiopaque parts will be clearly visible in the CT images (see FIG. 3). In some cases the main axis of each restorative element e.g. tooth is marked by drilling a cylindrical shaft. Incorporation of the scanning template in the CT images enhances the surgeon's ability to plan in function of the desired prosthetic outcome.

Following production of the scan template, the patient is sent to a radiologist for a CT scan. The scan template is placed in the patient's mouth and the scan is taken. The output of the scan is a stack of 2D slices forming a three-dimensional "data set".

Once the CT scan has been taken and the 3D models constructed (see FIG. 4), the surgeon plans the implant treatment using a computer program. Typically, such a program imports the data set provided by the radiology site without altering any information. Using image-processing techniques (e.g. image segmentation) three-dimensional models of the bone are derived from the data set. Given that the radiopaque dentition is well represented in the 2D axial slices, a 3D model of the desired prosthetic set-up can also be constructed.

Instead of using a radiopaque scan prosthesis, sometimes the diagnostic wax-up or a loose prosthesis is digitized separately (via CT, optical scanning or mechanical scanning) and afterwards registered to the anatomical structures visible in the volume data. This way information about the desired dentition is also obtained, in its correct relation relative to the jaw. The computer program (see FIG. 5) allows the individual patient's CT images to be assessed in a three-dimensional way and to determine where dental implants can be placed ideally. Implants can be chosen from a digital implant library (different implant brands, lengths, diameters, etc.).

The practitioner next defines a panoramic curve in the axial images (see FIG. 6). The curve typically follows the arch of the jaw. Several cross sections (see FIG. 7) can be chosen perpendicular to both the panoramic curve and the axial slices. Typically implant receptor sites are chosen in these cross sections. The practitioner can modify the positions and inclinations of each implant as needed in any of the views (axial, panoramic, 3D or cross sectional). Fine tuning is done by shifting and tilting of the implant representations or by changing their dimensions. Each individual implant position can be evaluated in terms of the volume of available bone, described as the "triangle of bone" by Ganz (Ganz S D, The triangle of bone—A formula for successful Implant Placement and Restoration, The implant society, Inc. 1995 Vol. (5); 5 pp 2-6). The quality of the bone is visualized in the computer program using, for example, Hounsfield units as a measure for bone density.

Once the implant plan has been fixed, the surgeon must transfer it as accurately as possible to the patient. This transfer can be done mentally, using custom made guiding templates, e.g. as supplied by Materialise, Leuven Belgium under the name SurgiGuide™ (see FIG. 8) or using alternative means of navigation.

Although the current computer programs for dental implant planning all visualize the information necessary to simulate different implant treatments and all offer a range evaluation tools, none provide automated or semi-automated assistance in determining the optimal position of the implants from a biomechanical, functional or aesthetic point of view.

SUMMARY OF THE INVENTION

A first object of the present invention is to provide improved methods for (semi-) automatic dental implant planning based on biomechanical, aesthetic and functional consideration, using volume data, e.g. from a volumetric scan. An advantage of the present invention is to overcome at least some of the disadvantages of the prior art.

According to a first embodiment of this first object, a method for preparing information for automated or semi-automated dental implant planning from image information relating to the jaw of a patient, comprises the steps of:
(a) generating 3D models of a tooth setup, and
(b) automatically detecting the constitutive restorative elements in the tooth setup.

Automatically detecting the constitutive restorative elements in the tooth setup may be done based image analysis such as based on grey scale values in the 3D model of the tooth set-up. Alternatively, automatically detecting the constitutive restorative elements in the tooth setup may be done by using the 3D model of the setup and detection on the basis of surface curvature analysis. Restorative element are artificial teeth and the like. The term "image analysis" is to be understood as the extraction of useful information from processible images capable to be displayed, preferably from digital images, by means of image processing techniques, preferably digital image processing techniques. Images of an object may include 2D slices of an object containing grey value information as well as any 3D representation providing insight in the spatial build-up of the object.

According to a second embodiment of this first object, a method for preparing information for automated or semi-automated dental implant planning from image information relating to the jaw of a patient, comprises the steps of:
(a) generating 3D models of parts of the jaw, and
(b1) detecting anatomical and artificial elements in the jaw bone, and
(b2) automatically selecting zones in the jaw where implants can or cannot be placed. The selection may be done by image analysis such as based on grey-scale value in the 3D model of the parts of the jaw. Anatomical elements to be detected may be nerves, blood vessels, cysts, impacted teeth, bone marrow, diseased bone or similar elements Artificial elements may be crowns, bridges implants, fillings, grafts, titanium membranes and the like.

According to some embodiments of the present invention, the method may further comprise the steps of:
(c) determining candidate implant dimensions, positions, orientations and configurations,
(d) obtaining implant plans,
(e) comparing implant plans to each other or to given criteria,
(f) selecting or improving an implant plan.

According to some embodiments of the present invention, the method may further comprise:
generating 3D models of parts of the jaw,
detecting anatomical and artificial elements in the jaw bone based on grey-scale value in the 3D model of the parts of the jaw and automatically selecting zones in the jaw where implants can or cannot be placed,
determining candidate implant dimensions, positions, orientations and configurations,
obtaining implant plans,
comparing implant plans to each other or to given criteria, and selecting or improving an implant plan.

According to some embodiments of the present invention, the step of generating 3D models of a tooth setup further may comprise a separately digitizing the desired tooth-setup and positioning it correctly with respect to the jaw by means of registration.

According to some embodiments of the present invention, the step of generating 3D models of a tooth setup may further comprise the positioning and scaling of teeth or tooth arches from a digital library relative to the jaw of the patient in volume images or in 3D.

According to some embodiments of the present invention, in the step of generating 3D models of parts of the jaw, image objects corresponding to natural or artificial teeth in the jaw may be detected.

According to some embodiments of the present invention, the step of generating 3D models of parts of the jaw may comprise the steps of:
slicing the 3D model of the jaw into a number of 2D slice images,
generating a panoramic curve for each of the 2D slice images,
evaluating in each slice image if one or more 2D features are present along the panoramic curve, and
combining the information of multiple slices to confirm the presence of a tooth.

According to some embodiments of the present invention, the step of generating a panoramic curve, the panoramic curve may be calculated as the midline of the contour in the slice of the jaw.

According to some embodiments of the present invention, the evaluating step may include the calculating of a correlation value between 2D matrices or features representing possible cross-sectional shapes of a tooth or tooth root and the grey-scales in local areas of the 2D slice images along the panoramic curve.

According to some embodiments of the present invention, the step of generating 3D models of parts of the jaw may further comprise an identification of zones of the jaw corresponding to the positions of individual teeth and attributing to the identified zones the respective tooth numbers based on mean tooth width values and known dimensions of the jaw. Possibly the identified zones may be corrected based on known positions of natural or artificial teeth.

According to some embodiments of the present invention, the step of detecting restorative elements in the tooth setup may include calculating the local surface curvatures of 3D model of the tooth setup, and subdividing the tooth setup in less complex regions or patches using a watershed algorithm based on the obtained curvature values.

According to some embodiments of the present invention, the step of detecting restorative elements in the tooth setup may comprise calculating of correlation values between 3D matrices or features representing possible tooth shapes and local surface areas on the 3D tooth setup model, and separating those surface areas where the correlation value exceeds a given threshold.

According to some embodiments of the present invention, the step of determining candidate implant dimensions, positions, orientations and configurations may comprise:

defining point grids on respectively the incisal/occlusal and the apical sides of the restorative elements, connecting for each element, all points of the incisal/occlusal grid with all points of the apical grid, determining the intersection points of the obtained axes with the 3D model of the bone, placing implants from a digital implant library along the respective axes with the implant shoulders at a given distance from the entry point of the axes in the bone, listing all possible combinations going from a minimum of one set of alternatives for a single implant for the entire tooth setup to a maximum of all alternatives for an implant for each restorative element in the tooth setup.

Possibly, according to some embodiments of the present invention, in the step of defining point grids, hollow operations may be used on the restorative elements to create 3D volumes representative of the metal base structure of the desired prosthesis. These volumes may be projected onto the 3D model of the restorative elements to give the outlines of said incisal/occlusal and apical point grids.

According to some embodiments of the present invention, in the step of defining point grids, projection contours of the restorative elements may be determined in the incisal/occlusal and apical planes, defined in the intersection points of the restorative elements with their respective apico-incisal axes, which projected contours are offset inwards providing an offset contour, the enclosed surface area of the offset contour in 2D is a given fraction of the original surface of the projected contour area and afterwards, the offset contour is projected back onto the restorative elements to yield the contours of said point grids.

According to some embodiments of the present invention, the projection may be done in the direction of the respective apico-incisal axes. According to some embodiments of the present invention, the apico-incisal axis of a restorative element may be determined as its principal axis of inertia.

According to some embodiments of the present invention, in the step of determining candidate implant dimensions, positions, orientations and configurations, an expert system is used to identify the type of implant case being treated and to suggest a typical corresponding implant plan based on the "best fit" of solutions in the expert system.

According to some embodiments of the present invention, the step of obtaining implant plans comprises assigning scores to the implant combination(s) in function of measurements performed relative to the volume images of the patient or to the 3D models created in the step of creating 3D models of a tooth set up or of parts of the jaw. According to some embodiments of the present invention, the shortest distances may be calculated between implants and the 3D models of the nerve, blood vessels and the jaw and in that the mean grey values of the voxels occupied by and in the immediate vicinity of the implants are determined along the implant axes.

According to some embodiments of the present invention, the step of obtaining implant plans may comprise assigning scores to the implant combination(s) in function of the predicted loads on the implants using a biomechanical or finite element model of the jaw, implants and prosthesis. Possibly, according to some embodiments of the present invention, the step of obtaining implant plans may comprise assigning scores to the implant combination(s) in function of the achievable emergence profiles for individual implants. Possibly, the achievable emergence profile may be expressed in function of the distance in a cross sectional view between the most buccal point of the implant shoulder and an axis through the most buccal point of the apical point grid in the section and a point situated at given apical and lingual distances from this point, which apical and lingual distances may preferably be respectively 3 mm and 2 mm for frontal teeth and 1 mm and 2 mm for distal teeth. According to some embodiments of the present invention, the distinction between frontal and distal teeth may be made by indicating a smile line in the volume images or on the 3D models.

According to some embodiments of the present invention, the step of comparing implant plans to each other or to given criteria further may comprise incrementally adjusting individual implant dimensions, positions and orientations in according to a predetermined strategy until the planning score reaches a given threshold value.

According to a preferred embodiment of the invention, an automatic or semi-automatic dental implant planning involves using one or more automated methods to determine or verify the optimal amount, dimensions, position, direction and configuration of dental implants in the bone of the patient. These methods are computer driven and are preferably unequivocal. The methods are based on predefined rules that relate to biomechanical considerations (e.g. quantity of bone, quality of bone, etc.) and aesthetical considerations (e.g. shape of the tooth, emergence profile, etc.).

According to the present invention, (semi-) automatic surgical planning and simulation may be accomplished using a computer. Accordingly patients may be scanned to obtain 3D volume image data. Computerized automatic or semi-automatic virtual implant placement may be performed on a computerized jaw model. The planning may afterwards be transferred to the patient by means of a surgical guide.

It is a feature of the present invention that the presence and positions of teeth (e.g. natural or artificial) are automatically recognized in the volume image data of the patient or on a three-dimensional model of the jaw. At that point, it is clear where the teeth can be found. Conversely, the missing teeth can now be identified and replaced by implants.

Another feature of the present invention is that implant dimensions, positions and directions are automatically or semi-automatically proposed and/or verified based on a known position of a prosthetic element relative to the bone of the patient.

It is also a feature of the present invention that implant dimensions, positions, directions and configurations (i.e. the inter-implant relationships) are automatically proposed and or verified from the known 3D geometry of the bone of the patient and/or from mathematical, biomechanical calculations taking into account the measured quality of the bone visible as grey values in the volume image data of the patient.

A significant advantage of the present invention is that clinicians are substantially aided in deciding on a treatment plan by having unambiguous guidelines implemented on a patient specific basis. The invention also constitutes a considerable saving in time given that a lot of criteria can be verified in a fraction of the time of what would be required if done manually.

A second object of the present invention is to provide a system for preparing information for (semi-) automatic dental implant planning based on biomechanical, aesthetic and functional consideration, using volume data, e.g. from a volumetric scan.

According to a first embodiment of the second object of the present invention, a system for preparing information for automated or semi-automated dental implant planning from image information relating to the jaw of a patient comprising:
  (a) means for generating 3D models of a tooth setup, and
  (b) means for automatically detecting restorative elements in the tooth setup based on image analysis.

The means for automatically detecting restorative elements in the tooth setup may automatically detect the constitutive restorative elements in the tooth setup based on grey scale values in the 3D model of the tooth set-up. Alternatively, the means for automatically detecting restorative elements in the tooth setup may automatically detect the constitutive restorative elements in the tooth by using the 3D model of the setup and detection on the basis of surface curvature analysis.

According to a first embodiment of the second object of the present invention, a system for preparing information for automated or semi-automated dental implant planning from image information relating to the jaw of a patient, comprising:
  (a) means for generating 3D models of parts of the jaw, and
  (b) means for detecting anatomical and artificial elements in the jaw bone and for automatically selecting zones in the jaw where implants can or cannot be placed based on image analysis.
The detecting may be based on grey scale values in the 3D model of the parts of the jaw According to embodiments of the present invention, the system further may comprise:
  (c) means determining candidate implant dimensions, positions, orientations and configurations,
  (d) means for obtaining implant plans,
  (e) means for comparing implant plans to each other or to given criteria,
  (f) means for selecting or improving an implant plan.

According to embodiments of the present invention, the system further may comprise:
  means for generating 3D models of parts of the jaw,
  means for detecting anatomical and artificial elements in the jaw bone based on grey scale values in the 3D model of the parts of the jaw and for automatically selecting zones in the jaw where implants can or cannot be placed,
  means for detecting restorative elements in the tooth setup,
  means for determining candidate implant dimensions, positions, orientations and configurations,
  means for obtaining implant plans,
  means for comparing implant plans to each other or to given criteria, and
  means for selecting or improving an implant plan.

According to embodiments of the present invention, the means for generating 3D models of a tooth setup further may comprise means for separately digitizing the desired tooth-setup and positioning it correctly with respect to the jaw by means of registration.

According to embodiments of the present invention, the means for generating 3D models of a tooth setup further may comprise means for positioning and scaling teeth or tooth arches from a digital library relative to the jaw of the patient in volume images or in 3D.

According to embodiments of the present invention, the means for generating 3D models of parts of the jaw may be characterized in that image objects corresponding to natural or artificial teeth in the jaw are detected.

According to embodiments of the present invention, the means for generating 3D models of parts of the jaw may comprise:
  means for slicing the 3D model of the jaw into a number of 2D slice images,
  means for generating a panoramic curve for each of the 2D slice images,
  means for evaluating in each slice image if one or more 2D features are present along the panoramic curve, and
  means for combining the information of multiple slices to confirm the presence of a tooth.

According to embodiments of the present invention, the means for generating a panoramic curve may calculate the panoramic curve as the midline of the contour in the slice of the jaw.

According to embodiments of the present invention, the mean for evaluating may include means for calculating a correlation value between 2D matrices or features representing possible cross-sectional shapes of a tooth or tooth root and the grey-scales in local areas of the CT slice images along the panoramic curve.

According to embodiments of the present invention, the means for generating 3D models of parts of the jaw may further comprise means for identifying zones of the jaw corresponding to the positions of individual teeth and attributing them the respective tooth numbers based on mean tooth width values and known dimensions of the jaw. The identified zones may be corrected based on known positions of natural or artificial teeth.

According to embodiments of the present invention, the means for detecting restorative elements in the tooth setup may include means for calculating the local surface curvatures of 3D model of the tooth setup, and subdividing the tooth setup in less complex regions or patches using a watershed algorithm based on the obtained curvature values.

According to embodiments of the present invention, the means for detecting restorative elements in the tooth setup may comprise means for calculating correlation values between 3D matrices or features representing possible tooth shapes and local surface areas on the 3D tooth setup model, and separating those surface areas where the correlation value exceeds a given threshold.

According to embodiments of the present invention, the means for determining candidate implant dimensions, positions, orientations and configurations comprises: means for defining point grids on respectively the incisal/occlusal and the apical sides of the restorative elements, means for connecting for each element, all points of the incisal/occlusal grid with all points of the apical grid, means for determining the intersection points of the obtained axes with the 3D model of the bone, means for placing implants from a digital implant library along the respective axes with the implant shoulders at a given distance from the entry point of the axes in the bone, means for listing all possible combinations going from a minimum of one set of alternatives for a single implant for the entire tooth setup to a maximum of all alternatives for an implant for each restorative element in the tooth setup.

According to embodiments of the present invention, the means for defining point grids may include means for performing hollow operations on the restorative elements to create 3D volumes representative of the metal base structure of the desired prosthesis and means for projecting volumes onto the 3D model of the restorative elements to give the outlines of said incisal/occlusal and apical point grids. Possibly, the means for defining point grids projection contours of the restorative elements may include means for determining in the incisal/occlusal and apical planes, defined in the intersection points of the restorative elements with their respective apico-incisal axes, which projected contours are offset inwards providing an offset contour, the enclosed surface area of the offset contour in 2D is a given fraction of the original surface of the projected contour area and afterwards, the offset contour is projected back onto the restorative elements to yield the contours of said point grids. Possibly the projection may be done in the direction of the respective apico-incisal axes. The apico-incisal axis of a restorative element may be determined as its principal axis of inertia.

According to embodiments of the present invention, the means for determining candidate implant dimensions, positions, orientations and configurations may include an expert system to identify the type of implant case being treated and to suggest a typical corresponding implant plan based on the "best fit" of solutions in the expert system. Possibly, the means for obtaining implant plans comprises means for assigning scores to the implant combination(s) in function of measurements performed relative to the volume images of the patient or to the 3D models created in the step of creating 3D models of a tooth set up or of parts of the jaw. The shortest distances may be calculated between implants and the 3D models of the nerve, blood vessels and the jaw and in that the mean grey values of the voxels occupied by and in the immediate vicinity of the implants are determined along the implant axes.

According to embodiments of the present invention, the means for obtaining implant plans may comprise means for assigning scores to the implant combination(s) in function of the predicted loads on the implants using a biomechanical or finite element model of the jaw, implants and prosthesis.

According to embodiments of the present invention, the means for obtaining implant plans may comprise means for assigning scores to the implant combination(s) in function of the achievable emergence profiles for individual implants. The achievable emergence profile may be expressed in function of the distance in a cross sectional view between the most buccal point of the implant shoulder and an axis through the most buccal point of the apical point grid in the section and a point situated at given apical and lingual distances from this point. The apical and lingual distances may be respectively 3 mm and 2 mm for frontal teeth and 1 mm and 2 mm for distal teeth. The distinction between frontal and distal teeth may be made by indicating a smile line in the volume images or on the 3D models.

According to embodiments of the present invention, the means for comparing implant plans to each other or to given criteria may further comprise means for incrementally adjusting individual implant dimensions, positions and orientations in according to a predetermined strategy until the planning score reaches a given threshold value.

The above-described method embodiments of the present invention may be implemented in a system, e.g. a processing system 100 such as shown in FIG. 30. FIG. 30 shows one configuration of processing system 100 that includes at least one programmable processor 103 coupled to a memory subsystem 105 that includes at least one form of memory, e.g., RAM, ROM, and so forth. It is to be noted that the processor 103 or processors may be a general purpose, or a special purpose processor, and may be for inclusion in a device, e.g., a chip that has other components that perform other functions. Thus, one or more aspects of the present invention can be implemented in digital electronic circuitry, or in computer hardware, firmware, software, or in combinations of them. The processing system may include a storage subsystem 107 that has at least one disk drive and/or CD-ROM drive and/or DVD drive. In some implementations, a display system, a keyboard, and a pointing device may be included as part of a user interface subsystem 109 to provide for a user to manually input information. Ports for inputting and outputting data also may be included. More elements such as network connections, interfaces to various devices, and so forth, may be included, but are not illustrated in FIG. 30. The various elements of the processing system 100 may be coupled in various ways, including via a bus subsystem 113 shown in FIG. 30 for simplicity as a single bus, but will be understood to those in the art to include a system of at least one bus. The memory of the memory subsystem 105 may at some time hold part or all (in either case shown as 111) of a set of instructions that when executed on the processing system 100 implement the steps of the method embodiments described herein. Thus, while a processing system 100 such as shown in FIG. 30 is prior art, a system that includes the instructions to implement aspects of the methods for obtaining information for or for optimising of the lithographic processing of a substrate is not prior art, and therefore FIG. 30 is not labelled as prior art.

The present invention also includes a computer program product which provides the functionality of any of the methods according to the present invention when executed on a computing device. Such computer program product can be tangibly embodied in a machine readable storage medium carrying machine-readable code for execution by a programmable processor. The present invention thus relates to a machine readable storage medium carrying a computer program product that, when executed on computing means, provides instructions for executing any of the methods as described above. The term "machine readable storage medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

According to a third object of the present invention, a computer program product including code for preparing information for automated or semi-automated dental implant planning from image information relating to the jaw of a patient, which, when executed on a computer system comprises:

(a) means for generating 3D models of a tooth setup, and (b) means for automatically detecting constitutive restorative elements in the tooth setup based on image analysis.

The means for automatically detecting constitutive restorative elements in the tooth setup may automatically detect constitutive restorative elements in the tooth setup based on grey scale values in the 3D model of the tooth set-up. Alternatively, the means for automatically detecting restorative elements in the tooth setup may automatically detect the constitutive restorative elements in the tooth by using the 3D model of the setup and detection on the basis of surface curvature analysis.

According to some embodiments of the present invention, the computer program product including code for preparing information for automated or semi-automated dental implant planning from image information relating to the jaw of a patient, which, when executed on a computer system comprises:

(a) means for generating 3D models of parts of the jaw, and
(b) means for detecting anatomical and artificial elements in the jaw bone and for automatically selecting zones in the jaw where implants can or cannot be placed based on image analysis.

The image analysis my be such that the detecting is based on grey scale values in the 3D model of the parts of the jaw. Optionally, the computer program product may include code for providing any of the means defined in any of the system according to the second object of the present invention.

According to a fourth object of the present invention, a machine readable storage medium storing the computer program product according to the third object of the present invention is provided.

These and further objects, features and advantages of the invention will become apparent from the following detailed description wherein reference is made to the figures in the accompanying drawings.

BRIEF DESCRIPTION OF THE FIGURES

The drawings described are only schematic and are non-limiting. In the drawings, the size of some elements may be exaggerated and not drawn on scale for illustrative.

FIG. 26 shows a 3D model of a jaw (2) with a patch or surface region (39) in the shape of a tooth;

FIG. 27 shows a 3D feature in the shape of a tooth; and

FIG. 28 is a schematic flow diagram of a method in accordance with an embodiment of the present invention.

DETAILED DESCRIPTION OF THE ILLUSTRATIVE EMBODIMENTS

The present invention will be described with respect to particular embodiments and with reference to certain drawings but the invention is not limited thereto but only by the claims.

Finding Optimal Implant Positions

Figure 1:
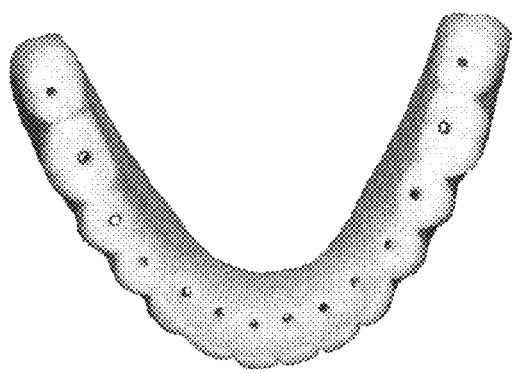
FIG. 1 shows a diagnostic wax-up manufactured to represent the desired tooth set-up.
Figure 2:
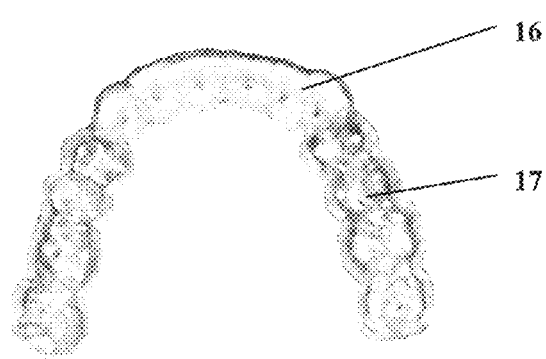
FIG. 2 shows a scan prosthesis that is placed in the mouth of the patient during CT scanning and has a number of radio-opaque elements.
Figure 3:
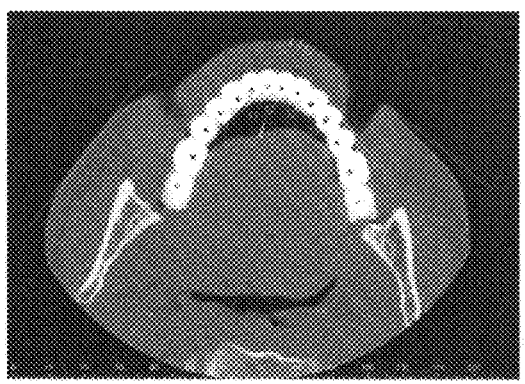
FIG. 3 shows an axial CT slice with a radio-opaque tooth set-up visible in the image.
Figure 4:
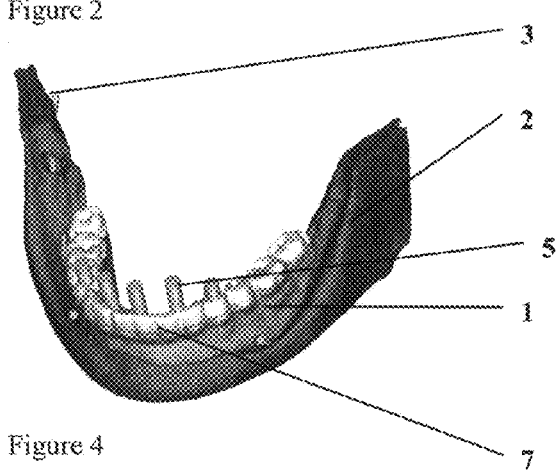
FIG. 4 shows the 3D models of an edentulous jaw (2), a corresponding tooth set-up (1) with several prosthetic elements (7) and of a nerve (3); it also shows the restorative space (5) of several planned implants.
Figure 5:
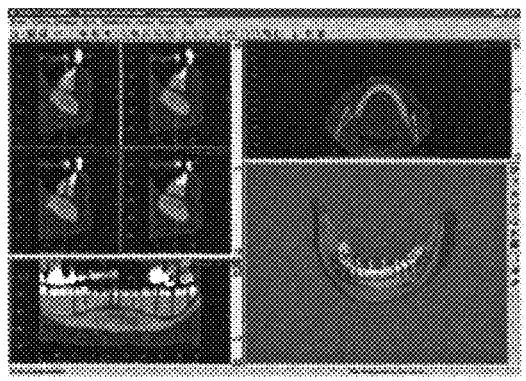
FIG. 5 shows a digital planning environment for dental implantology.
Figure 6:
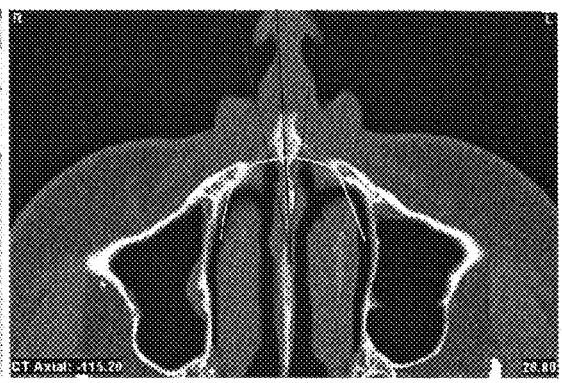
FIG. 6 shows a panoramic curve visualised in an axial CT scan image.
Figure 7:
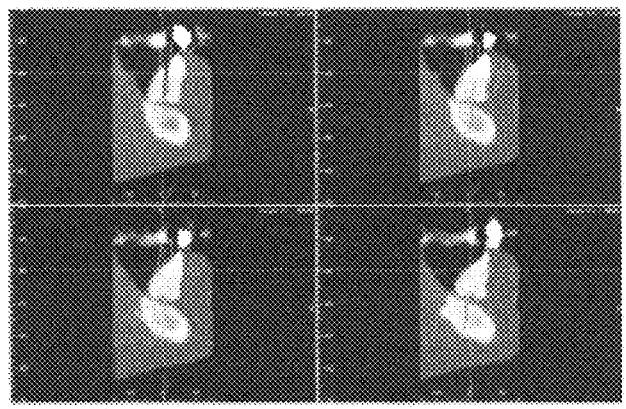
FIG. 7 shows a number of cross sectional views of a jaw and scan prosthesis.
Figure 8:
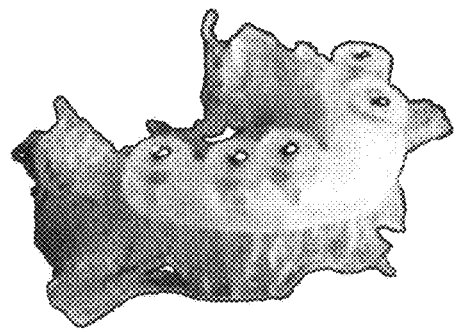
FIG. 8 shows a surgical template (SurgiGuide™), used to transfer a digital planning to the patient.

According to a preferred embodiment of the invention a three-dimensional representation of the desired tooth setup (1) and the jaw (2) and any nerves (3) or blood vessels is required and obtained (see FIG. 4). The methods for preparing information for automated or semi-automated dental implant planning from image information relating to the jaw of a patient as subject of the present invention are to be understood as computer based methods for preparing information for automated or semi-automated dental implant planning from image information relating to the jaw of a patient.

A schematic overview of a method according to the present invention is shown in FIG. 28. The steps shown in this flow will be described in more detail below.

Figure 9:
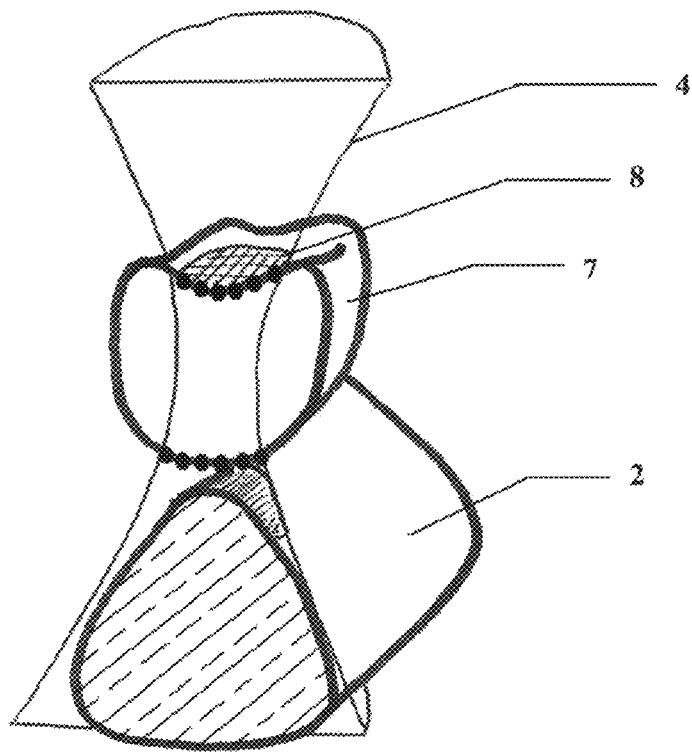
FIG. 9 shows a single prosthetic element (7) relative to the jaw (2) of the patient. The spatial boundaries (4) limiting the possible implant positions are dictated by two point grids (8) on the incisal/occlusal and apical surfaces of the prosthetic element (7)
Figure 14:
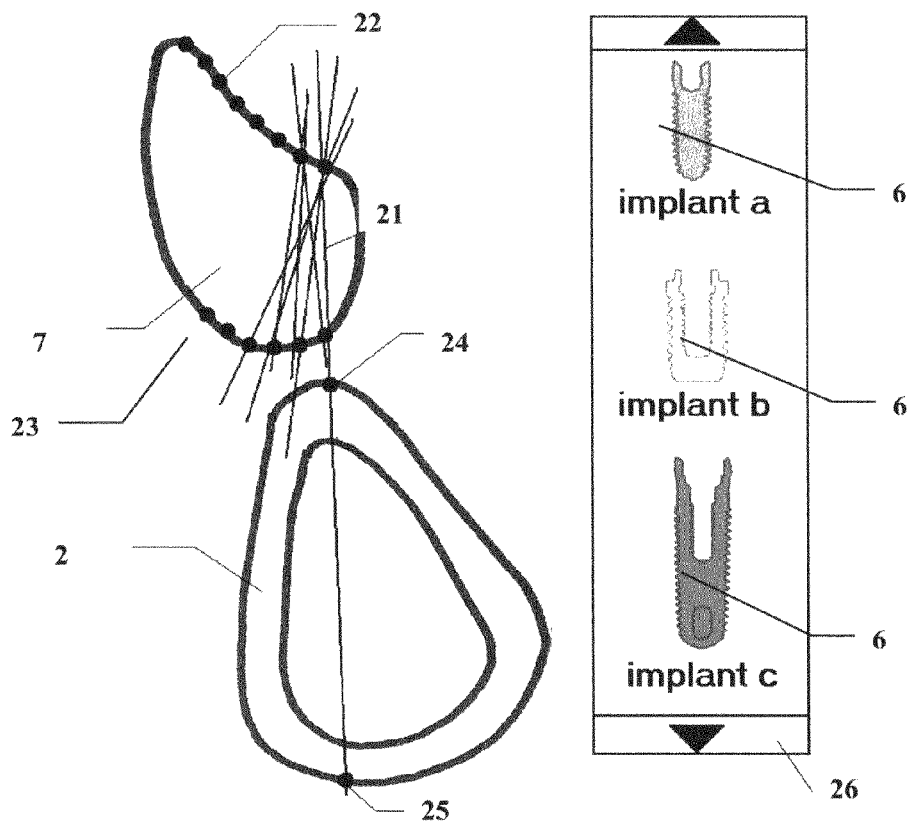
FIG. 14 shows a cross section of a prosthetic element (7) and the jaw (2). Potential implant axes (21), are defined by connecting points of the incisal/occlusal point grid (22) with points of the apical point grid (23). These axes (21) intersect the jaw (2) yielding entry points (24) and exit points (25). An implant library (26) lists possible implants (6)

The method starts when 3D models of parts of the jaw and/or 3D models of the tooth set-up are available, such as e.g. volumetric scans of the patient's jaw and a three-dimensional representation of the desired tooth setup (1) and the jaw (2) and any nerves (3) or blood vessels. In a first subsequent step (see FIG. 9), the 3D model of the tooth setup (1) is used to determine the spatial boundaries (4) to which the implants' restorative spaces (5) should ideally be confined in order to be aesthetically acceptable. A restorative space (5) is defined as the volume in space that would be occupied by an imaginary elongation of an implant (6) (see FIGS. 14 to 16) in the direction of the dental restoration. Spatial boundaries (4) can be identified for each element (e.g. tooth) (7) in the set-up (1). They can be defined in function of spatial point grids (8) on respectively the incisal/occlusal and the apical side of the elements 7 (projected on the surfaces or not). Several techniques can be used to define the grids (8). A number of illustrative techniques are listed hereafter.

Figure 10:
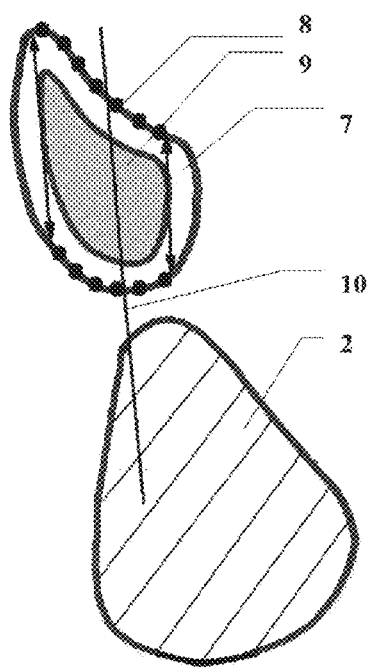
FIG. 10 shows a cross section of a prosthetic element (7) and the jaw (2), with the apico-incisal axis (10) passing through the internal offset (9) of the of the element.
Figure 11:
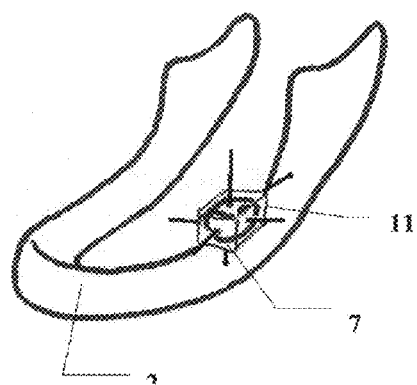
FIG. 11 shows the smallest bounding box (11) of a prosthetic element (7) relative to the lower jaw (2)

One option is to use an offset or hollow operation to create a 3D volume (9) (see FIG. 10) inside the 3D model of the tooth (7). This 3D volume (9) is representative of the metal base of the physical prosthesis onto which a porcelain layer is deposited to mimic the enamel of the teeth. The outlines of the grids on the surface of the 3D tooth model are obtained by projecting the obtained volume on it. Preferentially the direction of the projection is given by the apico-incisal axis (10) of the prosthetic element (7). The axis can be found for instance by calculating the smallest bounding box (11) (see FIG. 11) to still hold the prosthetic element and determining the distance from the prosthetic element to the jaw bone along each of the three principal axes of the bounding box. The axis yielding the shortest distance is the apico-incisal axis of the element. Alternatively the principal axes of inertia of the prosthetic element can be calculated. The apico-incisal axis will be the one along which the distance from the element to the bone is the shortest.

Figure 12:
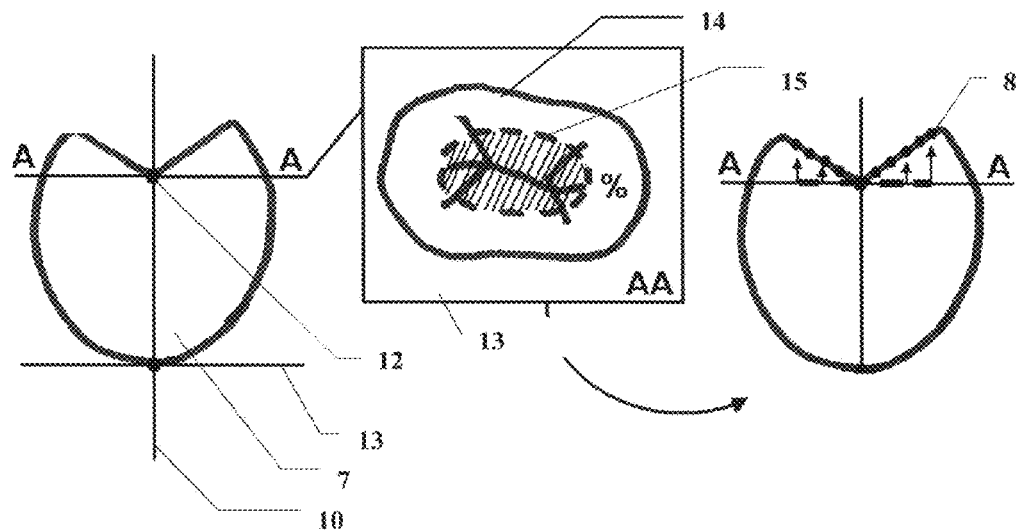
FIG. 12 shows a cross sectional and sectional view of a prosthetic element. The apico-incisal axis (10) intersects the element in two points (12), defining two planes (13) perpendicular to it. The contours (14) of the element in these planes (13) are offset (15) and project on the surface of the element, yielding a 3D contour of a point grid (8).

A second option to define the grids is to determine the two intersection points (12) of the element's apico-incisal axis with its surface (see FIG. 12). In these intersection points planes (13), the incisal/occlusal and apical plane, are defined perpendicular to the apico-incisal axis. In these planes the element is projected axially, yielding in each plane a closed 2D curve (14) or projected contour. Next, the total surface enclosed by these curves is calculated and the curves are offset inward until the enclosed surface reaches a given percentage of the original value. The thereby obtained 2D curves (15) or offset contours are projected back onto the element, outlining the contours of the respective point grids.

Another optional method to define the point grids (8) is by modifying the design of the scanning template (16). In this case the radio-opaque teeth (17) used to make the scanning template are regular or irregular shaped tubes with a limited wall thickness. When calculating the 3D model of the tooth setup from the CT images, the spatial boundaries (4) are readily identifiable in the 3D model as holes in the different elements of the tooth setup. The boundaries of these holes at the apical and incisal/occlusal side can be used as contours for the point grids. The grid surface is defined by hole filling this contour.

Figure 13:
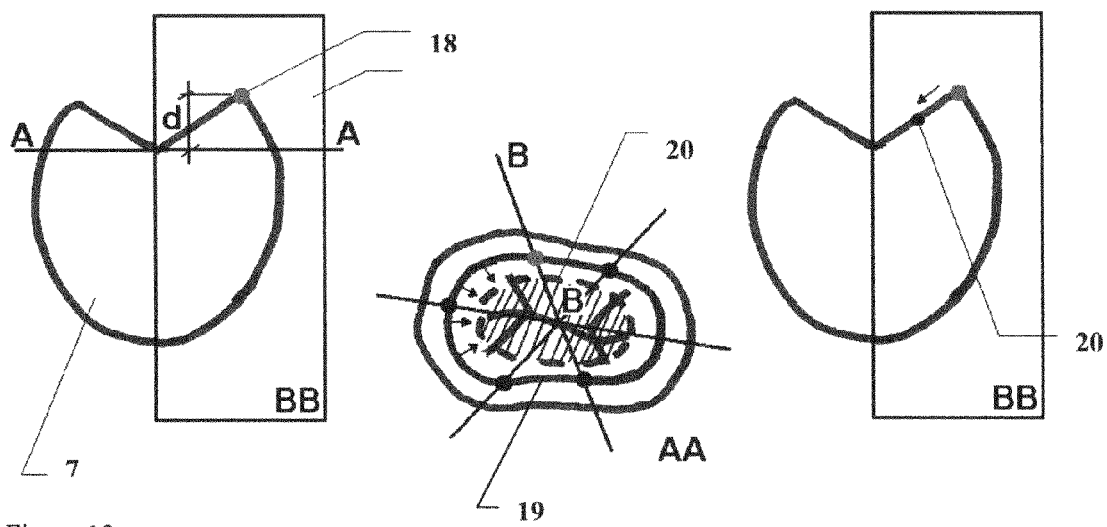
FIG. 13 shows a cross section and a cross sectional view of a prosthetic element. The most incisal/occlusal points (18) of in several radially oriented planes yield a contour (19) passing through the cusps of the tooth, which can be offset inward to yield the contour (20) of the point grid (8).

Yet another way to define the outline of the point grid (8) on the incisal/occlusal side of the elements is to calculate the intersection point (12) of the element with the apico-incisal axis (10) (see FIG. 12), on the incisal/occlusal side of the element. Next a systematic search is performed in all directions radial to the apico-incisal axis for those points (18) (see FIG. 13) located in the most incisal/occlusal positions (d) with respect to the intersection point. Thus a 3D curve is defined on the surface of the elements, which connects the cusps of the tooth. Seen that these cusps should remain imperforated, the 3D curve (19) is offset inward on the element's surface. The offset curve (20) can now be used as contour for the point grid (8).

The latter technique is particularly useful when dealing with molars and premolars.

In a second step the point grids (8), which have been identified on the different elements (7) of the tooth setup (1), are used to identify the potential implant axes (21) (see FIG. 14)). For each element (7) in the tooth setup (1), optionally all points of the incisal/occlusal grid (22) can be connected to all points of the apical grid (23). Thereby a finite number of sets of implant axes (21) are obtained for each element. All axes are aesthetically acceptable. Guidelines may be used to stipulate the size of the point grids at the apical side of the tooth relative to the incisal/occlusal side. For instance, the point grid surface at the apical side may be approx. 1.5 mm smaller all-round compared to at the incisal/occlusal side. Thereby sufficient space is available for metal and porcelain when the lab technician fabricates the restoration. In a molar, the apical point grid will likely be oval in shape, while for an incisor it may be reduced to no more than a single centre point.

As a third step, the intersections of each axis with the 3D bone model are calculated. Thereby the entry (24) and exit points (25) on the bone are known (see FIG. 14). Next, the implants (6), available for example from an implant library (26) are placed respectively according to each of axes' directions, with implant centre line passing through the respective entry points. For example, shoulders of the implants (27) are positioned at a given distance (e) relative to the entry points (24) (see FIG. 15). This distance can vary depending on the implant design. For each of the implants, in each position, checks are performed in order to score the solution. Scoring a solution means providing one or more goodness of fit criteria and one or more goodness of fit values for this/these criterion/criteria.

Figure 15:
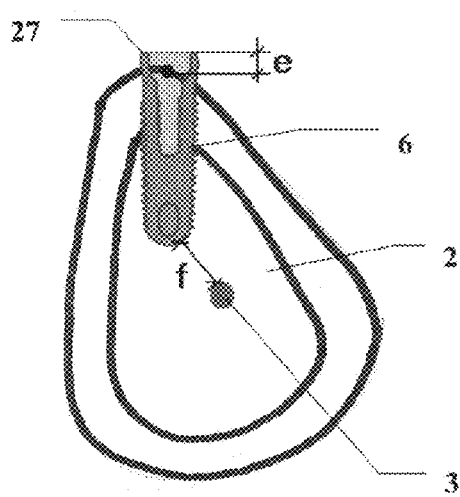
FIG. 15 shows an implant (6) with unicortical fixation, positioned at a distance f with respect to a nerve (3), and with its implant shoulder (27) at distance e relative to the entry point in the jaw (2)
Figure 16:
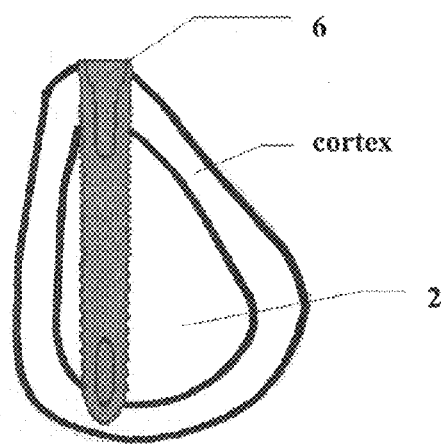
FIG. 16 shows an implant (6) with a bicortical fixation.
Figure 17:
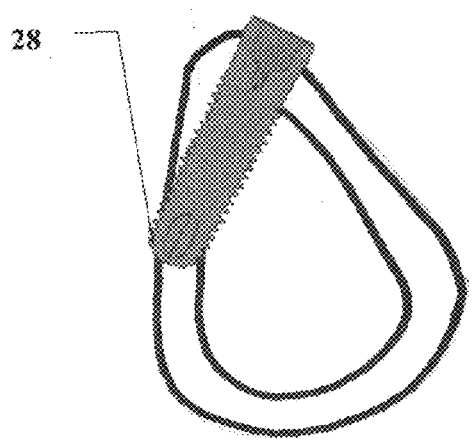
FIG. 17 shows jaw with a fenestration (28) by an implant.

In one embodiment of the present invention, the total score of a suggested solution can be regarded as the weighted average of the individual scores for some or for each check. Such checks may be:

The proximity (f) of the implant model to the 3D model of a nerve or blood vessel (see FIG. 15);

The extent to which the implant is centered in the bone (see FIG. 17). This includes, for instance, a check to see whether fenestrations (28) occur i.e. perforations of the bone in a place other than the entry point;

The quality of the bone around the implant, expressed for instance by the mean gray values of the voxels occupied by and in the immediate vicinity of the implant (6) in a volumetric image such as a CT image;

The extent to which the axis of the implant is centered in the contour of the incisal/occlusal point grid, the implants' long axis should preferably emerge in the centre of the occlusal surface of the teeth;

The presence of a uni- or bicortical (see FIG. 16) fixation; e.g. to surround the implant with a maximum volume of bone;

The position of the shoulder of the implant relative to the surface of the bone (ideally between 1.5 and 2 mm above bone level);

The direction of the implant relative to the direction of occlusal forces. For stress distribution, it is best to consider occusal forces to be directed along the axis of the implant instead of oblique to it;

Type of surface finish of the implant (rough/polished)

Type of implant connection (internal or external; hexagon or octagon, etc.).

It is clear that scoring may differ in function of the type of restoration preferred by the patient or the treating physician. The two main options are a screw retained prosthesis and a cemented prosthesis. Screw retained prostheses are attached directly onto the implants using small screws. The implants should therefore emerge as much as possible in the centres of the incisal/occlusal surfaces of the restorative elements and never, on the buccal (i.e. visible side) of the teeth.

Cemented prostheses are not placed directly on the implants. Instead an intermediary component known as an abutment is screwed on the implant and the prosthesis is cemented onto the abutments. The abutments can be used to change the original or planned direction of attachment to the implant by up to 45°. Implants can thus be planned for instance purely based on biomechanical considerations such as quantity and quality of the bone. During restorations, the direction of the implant emergence must be corrected for aesthetic purposes.

Some of the checks can be specific for or defined in function of a particular type of element (frontal vs. distal; incisor vs. canine, etc.). In these cases it is important to know the type of element on which the check is being performed. A typical example is the distinction between an element which will be visible when the patient smiles and an element which will not be visible.

Figure 18:
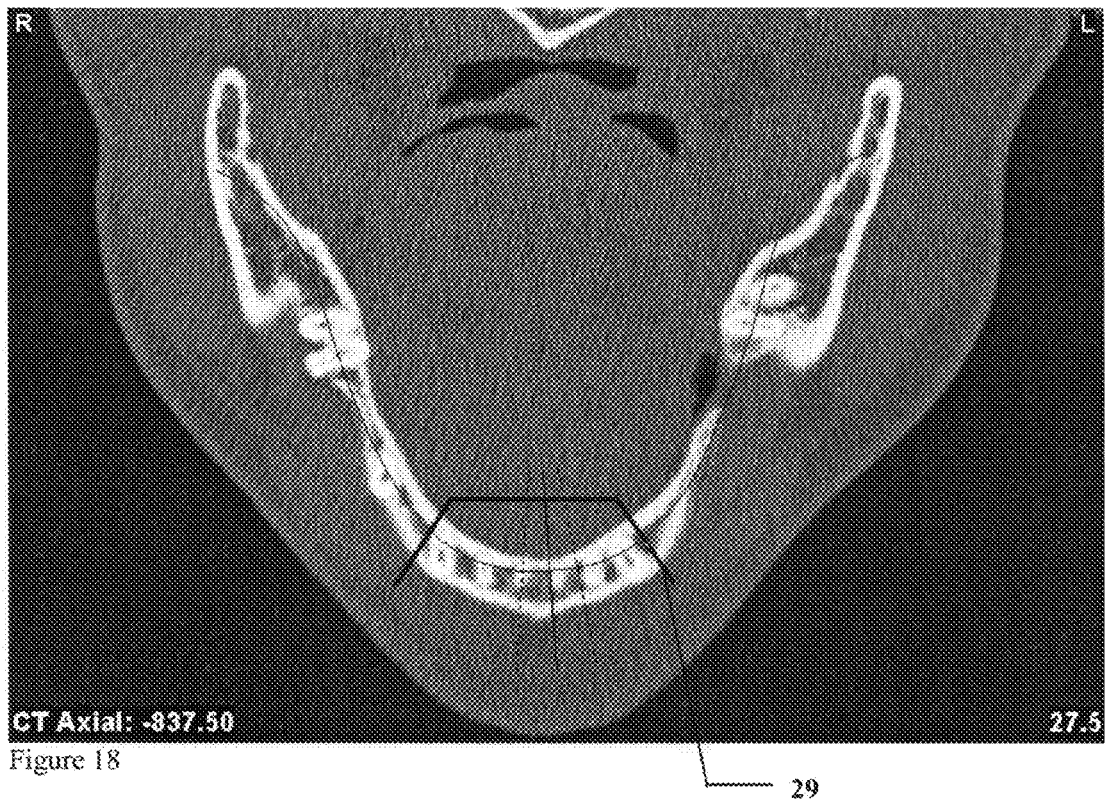
FIG. 18 represents a smile line (29) superimposed on the axial images of a CT scan.

It is an aspect of the current invention to incorporate in the planning environment a method to indicate the smile line (29) of the patient (see FIG. 18), which can be used to determine an optimal implant treatment. An illustrative method to indicate the smile line (29) consists of a bracket superimposed on the axial volumetric images, e.g. CT images, that can be moved by the physician to indicate the visible region. Another example is a tool allowing the physician to cut the 3D model of the tooth setup in order to divide it in a visible and a non-visible part.

Figure 19:
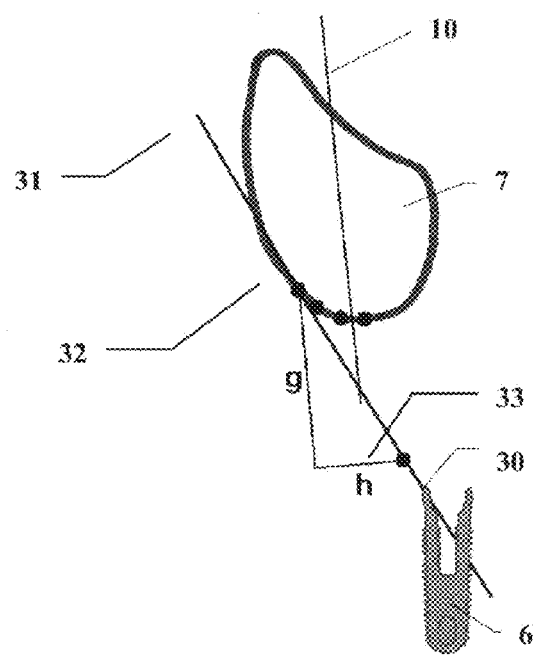
FIG. 19 shows the cross section of a prosthetic element (7) and an implant (6). The most buccal point (30) on the implant shoulder is located on a line (31) through the most buccal point (32) of the point grid in the given section and a point (33) situated g mm more apical and h mm more lingual.

An illustrative example of a check that depends on the tooth type pertains to the evaluation of the achievable emergence profile (i.e. describes the manner in the tooth erupts from the gums) in function of the implant position. The criterion used to perform the check is based on a cross sectional view of the restorative element (tooth) (7) and the implant (6) under evaluation (see FIG. 19). It states that implants have an ideal emergence profile when the most buccal point (30) of the implant shoulder is situated on the axis (31) running through the buccal intersection point (32) of the point grid contour with the section plane and a second point (33) situated a given apical (g) and lingual (h) distances from this intersection point. The latter distances are different for molars, premolars, incisors and canines.

Figure 20A:
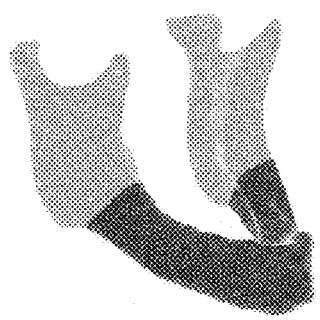
FIGS. 20a and 20b represent biomechanical models of the jaw with and without implants and superstructure.
Figure 20B:
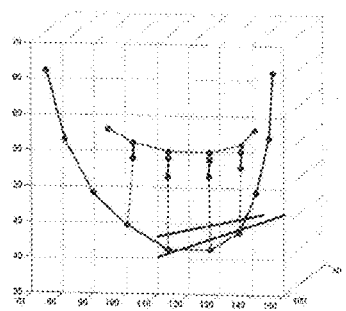

A fourth step consists of the evaluating the configuration of the implants (i.e. the positions and inclinations of the implants relative to each other). A limit can be set to the amount of different implant brands, lengths and/or diameters used for the treatment of a single patient. The distances between the implants are calculated automatically and compared to a given minimum distance that can differ for different implant systems. In addition a biomechanical (e.g. analytical) model (FIG. 20*a* and FIG. 20*b*) can be used to predict the loads on the implants as a result of mastication (e.g. several scenarios are used e.g. biting an apple, chewing gum, etc.). The model can take into account the deformation of the jaw (1) under loading, and/or the type and design of the prosthesis that will be attached to the implants (e.g. a stiffness value such as the E modulus of the material that will be used, and/or the moment of inertia in each section or a combination of the two), etc. Its predictions are used to determine the amount of required implants and the way the implants should be distributed over the potential implant sites. In a further aspect, starting from the implant configuration consisting of all implants with the highest individual scores, the configuration can be systematically modified by replacing one of the implants with its next best substitute (e.g. based on the individual scores) until all configuration criteria have been met.

Figure 21:
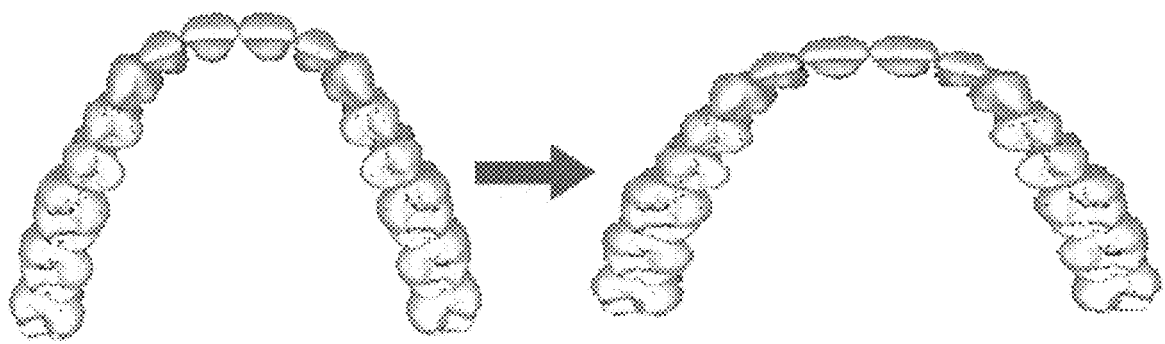
FIG. 21 represents a scalable tooth arch.

According to another embodiment of the invention the three-dimensional representation of the desired tooth setup is not available in the volumetric scans, e.g. CT scan images. Instead a library of scaleable teeth or tooth arch representations (FIG. 21) is used to represent the restorative elements. The library teeth or tooth arch can be superimposed on the volumetric, e.g. CT scan images to position them/it relative to the jawbone. The library teeth or tooth arch can also be seen in a 3D view relative to the 3D representations of the jaw (2), the nerves (3) and blood vessels. Further, the library teeth or tooth arches can be automatically scaled in function of the available space along the jaw. For example, the width of each library tooth along a predefined arch can be modified in such a manner that the sum of all tooth widths matches the length of the jaw as measured in projection.

For partially edentulous cases, the teeth or tooth arch available from the library can be registered to the 3D representations of the corresponding remaining teeth of the patient. Thereby an optimal fit can be obtained. The gaps between the remaining teeth are filled by proposed restorative elements coming form the tooth library. These library teeth are used further to perform the treatment planning, e.g. they can be included automatically. This approach has the advantage that the spatial boundaries for the restorative spaces of the implants or even potential implant axes can be predefined as part of the library. The process, optionally automated, of determining an adequate implant plan can thereby be considerably accelerated.

Alternatively a prosthesis or wax-up can be scanned optically and registered to the images or 3D of the jaw, thereby providing the required information about the desired tooth setup.

Finding Acceptable Implant Positions

According to yet another embodiment of the invention only a three-dimensional representation of the jaw (2) and any nerves (3) or blood vessels are used. The planning environment incorporates, for example, an expert system that holds a number of crisp or fuzzy rules for implant placement, based on an analysis of a database of sample implant planning cases in conjunction with experts' knowledge on implant treatment. Some of the rules are identification rules, used to distinguish between typical case types (e.g. a single implant between two neighboring teeth, a full arch reconstruction, two molars missing in the distal region), some rules are implant placement rules used to suggest implant types and configurations typical for treatment of a certain type of case (e.g. for a single implant between two neighboring teeth the position of the implant typically corresponds to the middle between the teeth). At the beginning of a planning case, the expert system will use the 3D representation of the jaw to identify the type of case and suggest a preliminary implant configuration corresponding to the "best fit" solution in the expert system.

In a next step the preliminary configuration is evaluated relative to the confinements imposed by the specific case (e.g. amount and quality of available bone in the suggested implant sites, proximity to nerves or blood vessels, presence of bone fenestrations, etc.). Each individual implant is required to meet a set of prerequisites in order to be accepted (e.g. at least 2 mm distance relative to the closest nerve, a maximum inclination relative to the cranio-caudal axis of the patient, etc.).

In a limited implementation of the embodiment, the system only provides feedback to the user about the acceptability of the suggested planning. The feedback could for instance be textual, with a message telling the user which implants should be reconsidered. Alternatively a colour code could be used to indicate either accepted implants (green) or refused implants (red). In accordance with this embodiment, user interaction is required to fine-tune the treatment plan.

In more advanced implementations of the embodiment, the system incrementally corrects the individual implant positions, orientations, length and diameters until the individual prerequisites are met. This constitutes a global optimization problem, e.g. identification of optimal values for multiple parameters, which can be solved for instance using a cost function such as a discrete cost function. Each individual parameter, e.g. position, length, angle, distance, orientation, etc., is associated with a scoring value. As the parameter is modified, for instance the angle of the implant is changed by 1°, the score of the parameter is updated. The scoring value can be determined based on the contribution of that parameter to increasing the favorability of the change as far as the implant is concerned. A weighted average value for the different scores can be used to evaluate the acceptability of the proposed implant plan.

Figure 22:
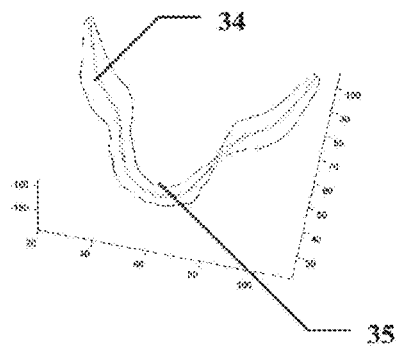
FIG. 22 shows a sectional contour (34) of a jaw with a corresponding panoramic curve (35)
Figure 23:
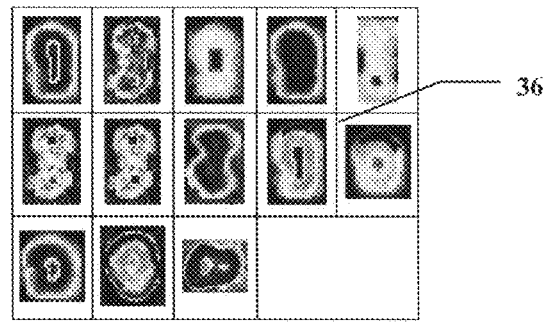
FIG. 23 shows a number of 2D features (36) in the shape of tooth roots and teeth.

The present intervention incorporates a method to automatically detect the presence and positions of teeth in the volume image data of the patient. In an illustrative embodiment of the method for this automated detection uses a 3D model of the jaw (2) as input in addition to the volume data itself. Firstly, the 3D model is digitally sliced to obtain a number of 2D slice images, i.e. a set of contours (34) with a given inter-slice distance (see FIG. 22). Next, a panoramic curve (35) is automatically generated for each of the contours. These panoramic curves can be calculated for instance as the midlines of the contours. Following the creation of the panoramic curves, a check is performed in each volumetric data slice, e.g. CT slice to evaluate whether or not a "feature" (36) is present along the panoramic curve (see FIG. 23). If the CT slices do not correspond to the slicing of the 3D model, interpolated images can be used. Features (36) are 2D matrices representing the possible shapes of a cross-section of a tooth or tooth root. A feature (36) is recognized for instance when a given correlation value becomes greater than a certain value. Alternatively a feature can be recognized when the element-wise product of the feature and the grey-scales in the CT slice exceeds a certain value.

Figures 24A, 24B:
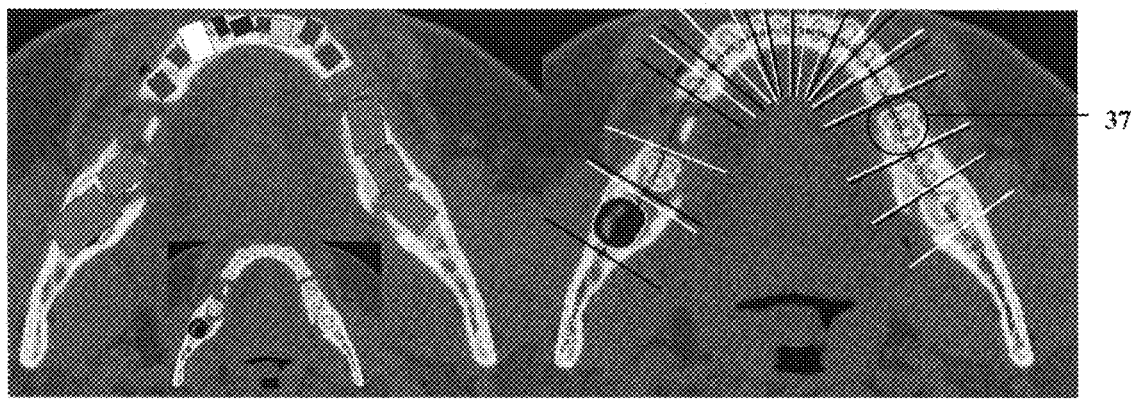
FIG. 24 shows a jaw in which a number of features have been recognized and which consequently has been split into several (37) that can be attributed to the positions of teeth.

When a feature has been recognized, a tooth number can be assigned for instance based on mean tooth width values (see FIGS. 24a and 24b). Zones on the jawbone (37) are attributed to the teeth that would typically occupy them. These zones are identified by adding up mean tooth width values starting from the middle of the panoramic curve. Corrections can be made based on the known arch length of the jaw or already identified teeth.

The result of the above operations is an automated tooth identification in each of the volumetric data slices, e.g. CT slices. Using the information gathered in all slides the presence of a tooth is either confirmed or not by verifying if a tooth has been identified in multiple CT slice.

Figure 25:
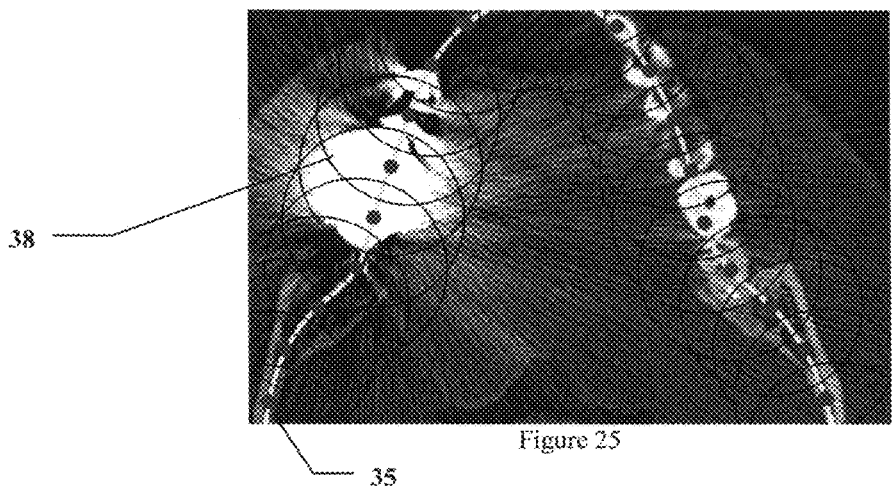
FIG. 25 shows an axial CT slice with scatter (38)

In addition each volumetric data slice, e.g. CT slice is checked with respect to the presence of scatter (38) (see FIG. 25). A typical check may entail looking at the Hounsfield values in the CT slice, and calculating the Fourier spectrum of the grey-values along a predefined curve (for instance a 2D offset of the panoramic curve). The black and white pattern typically associated with scatter results in one or more frequency peaks in the spectrum. Alternatively a check may be performed to see whether there are areas (of a predefined size) in the CT slice with a mean Hounsfield unit value exceeding a certain threshold. When deciding if a tooth is present or not, slices containing scatter can be treated in a dedicated manner (for instance by using weighing factors of certainty).

The present intervention also incorporates a method to automatically identify individual teeth in a 3D model of a scan prosthesis (16) or a 3D model of the jaw (2). In an illustrative embodiment of this method the complex 3D model of the jaw (2) or scan prosthesis (16) is broken up sequentially and subdivided into less complex and more identifiable regions or patches (39) (see FIG. 26, 27). This can be done for instance by using a watershed algorithm based on curvature calculations (Mohandas S., Henderson M., Pursuing mechanical part feature recognition through the isolation of 3D features in organic shapes, IMECE2002-DE-34419, ASME 2002—International Mechanical Engineering Conference and Expo November 17-22, New Orleans, La.). The patches are afterwards compared with a set of predefined 3D features representative of teeth (40). Features can be recognized for instance when a given correlation value becomes greater than a certain value.

It is a feature of the present invention that parts of the described methods can be used separately such as a method for automatic numbering of zones of the jaw, a method for recognizing teeth in a tooth setup, etc.

Figure 29:
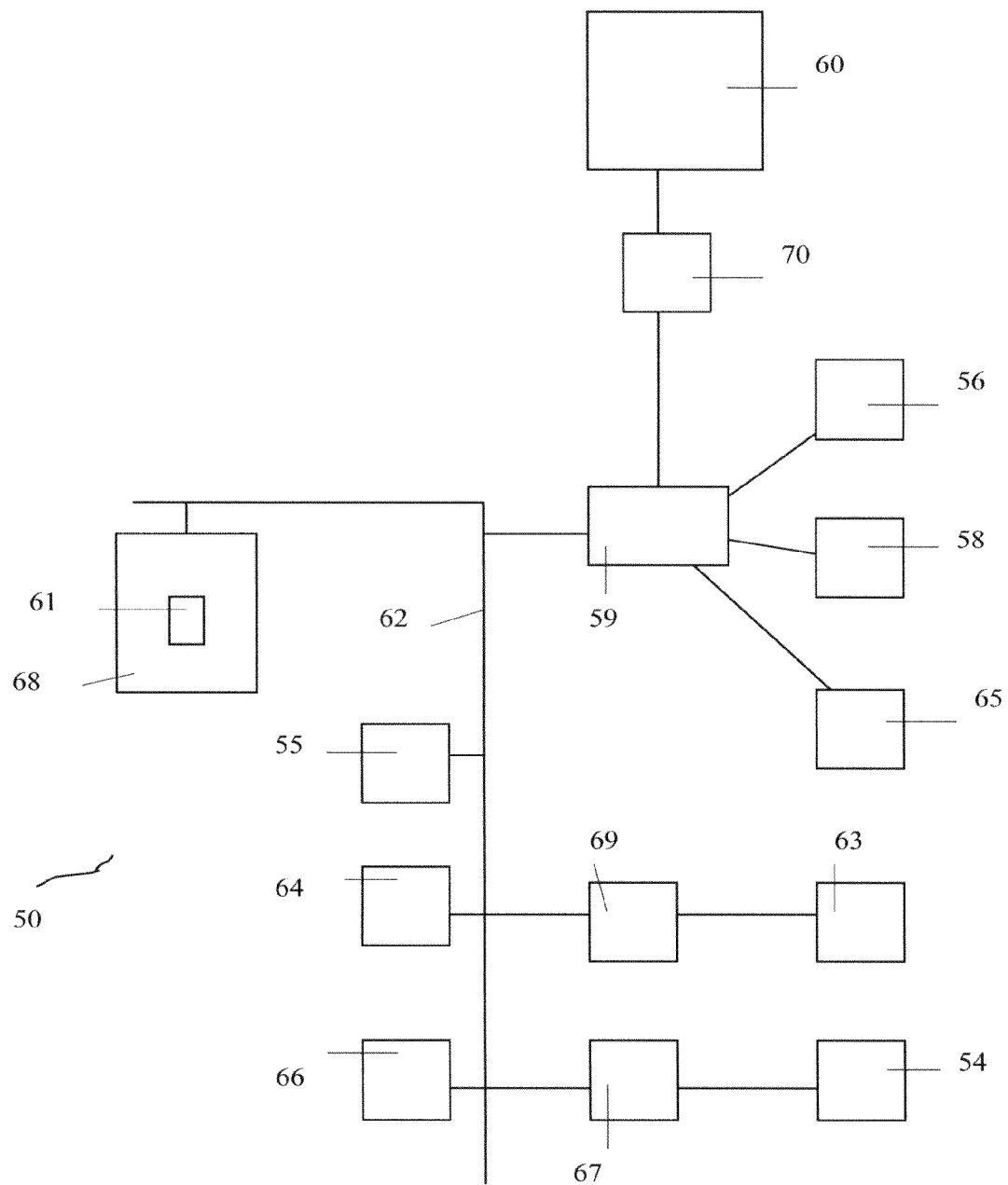
FIG. 29 is a schematic representation of a computer system in accordance with an embodiment of the present invention.
Figure 30:
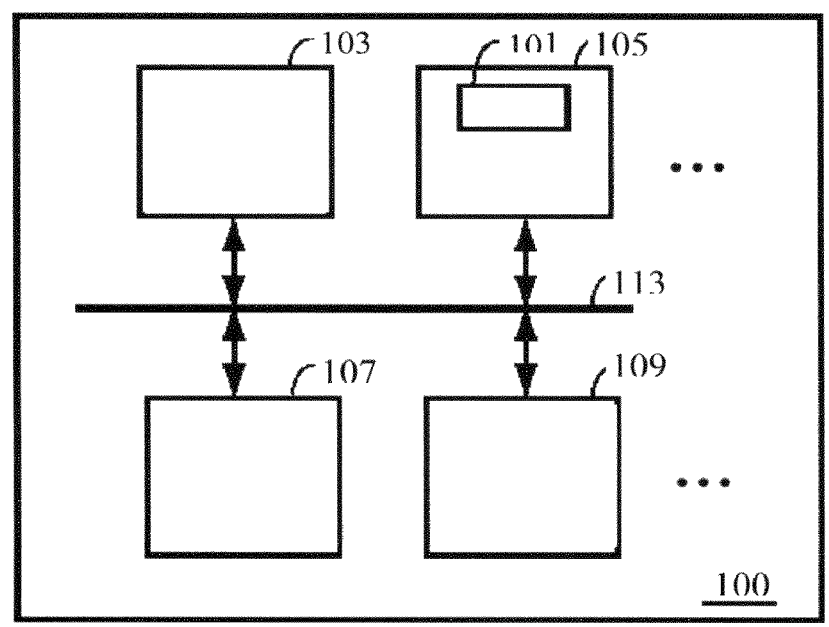
FIG. 30 shows a configuration of processing system for preparing information for automated or semi-automated dental implant planning from image information relating to the jaw of a patient.

FIG. 29 is a schematic representation of a computing system which can be utilized with the methods and in a system according to the present invention, e.g. the method shown in FIG. 28. A computer 50 is depicted which may include a video display terminal 54, a data input means such as a keyboard 56, and a graphic user interface indicating means such as a mouse 58. Computer 50 may be implemented as a general purpose computer, e.g. a UNIX workstation or a personal computer.

Computer 50 includes a Central Processing Unit ("CPU") 55, such as a conventional microprocessor of which a Pentium IV processor supplied by Intel Corp. USA is only an example, and a number of other units interconnected via bus system 62. The bus system 62 may be any suitable bus system—FIG. 29 is only schematic. The computer 50 includes at least one memory. Memory may include any of a variety of data storage devices known to the skilled person such as random-access memory ("RAM"), read-only memory ("ROM"), non-volatile read/write memory such as a hard disc as known to the skilled person. For example, computer 50 may further include random-access memory ("RAM") 64, read-only memory ("ROM") 66, as well as a display adapter 67 for connecting system bus 62 to a video display terminal 54, and an optional input/output (I/O) adapter 69 for connecting peripheral devices (e.g., disk and tape drives 63) to system bus 62. Video display terminal 54 can be the visual output of computer 50, which can be any suitable display device such as a CRT-based video display well-known in the art of computer hardware. However, with a desk-top computer, a portable or a notebook-based computer, video display terminal 54 can be replaced with a LCD-based or a gas plasma-based flat-panel display. Computer 50 further includes user interface adapter 59 for connecting a keyboard 56, mouse 58, optional speaker 65, as well as allowing optional physical value inputs from physical value capture devices such as medical imaging equipment 70 of an external system 60. System 60 may be connected to bus 62 a data network such as the Internet, an Intranet a Local or Wide Area network (LAN or WAN) or a CAN. The medical imaging equipment 70 may be any suitable equipment for capturing volumetric 3-D data of a patient's anatomy such as CT or MRI. This medical imaging equipment may include any device for capturing relevant volumetric image data of a patient. The data capturing device 70 of system 60 allows transmission of data relating to physical information of a patient to be transmitted over a telecommunications network, e.g. entering a volumetric description of a patient's anatomy at a remote location and transmitting it to a near location, e.g. via the Internet, where a processor carries out a method in accordance with the present invention.

The present invention also includes within its scope that the relevant volumetric data are input directly into the computer using the keyboard 56 or from storage devices such as 63, e.g. from a suitable signal storage medium such as a diskette, a replaceable hard disc, an optical storage device such as a CD-ROM or DVD-ROM, a magnetic tape or similar.

Computer 50 also includes a graphical user interface that resides within machine-readable media to direct the operation of computer 50. Any suitable machine-readable media may retain the graphical user interface, such as a random access memory (RAM) 64, a read-only memory (ROM) 66, a magnetic diskette, magnetic tape, or optical disk (the last three being located in disk and tape drives 63). Any suitable operating system and associated graphical user interface (e.g., Microsoft Windows, Linux) may direct CPU 55. In addition, computer 50 includes a control program 61 that resides within computer memory storage 68. Control program 61 contains instructions that when executed on CPU 15 allow the computer 10 to carry out the operations described with respect to any of the methods of the present invention.

Those skilled in the art will appreciate that the hardware represented in FIG. 29 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already described.

In the example depicted in FIG. 29, the computer program product for carrying out the method of the present invention can reside in any suitable memory. However, it is important that while the present invention has been, and will continue to be, that those skilled in the art will appreciate that the mechanisms of the present invention are capable of being distributed as a computer program product in a variety of forms, and that the present invention applies equally regardless of the particular type of signal bearing media used to actually carry out the distribution. Examples of computer readable signal bearing media include: recordable type media such as floppy disks and CD ROMs and transmission type media such as digital and analogue communication links.

Accordingly, the present invention also includes a software product which when executed on a suitable computing device carries out any of the methods of the present invention. In particular, the code includes any of the following (a) means for creating 3D models of a tooth setup (b) and/or means for creating 3D models of parts of the jaw, (c) means for detecting zones in the jaw where implants can (or optionally cannot be placed), (d) means for detecting restorative elements in the tooth setup, (e) means for determining candidate implant dimensions, positions, orientations and configurations, (f) means for obtaining implant plans, (g) means for comparing implant plans to each other or to given criteria, (h) means for selecting or improving an implant plan. Further code is provided for executing any of the methods or means provided by the present invention, e.g. as detailed in the appended claims.

The present invention also includes a computer product as defined above stored on a machine readable medium or media.

The invention claimed is:

1. A method for preparing information for automated or semi-automated dental implant planning from image information relating to the jaw of a patient, comprising:
   (a) generating 3D models of parts of the jaw bone, and
   (b1) detecting anatomical and artificial elements in the 3D model of the jaw bone based on image analysis, and
   (b2) automatically selecting zones in the 3D model of the jaw bone where implants can or cannot be placed, wherein the step of generating 3D models of parts of the jaw comprises the steps of:
   slicing the 3D model of the jaw into a number of 2D slice images,
   generating a panoramic curve for each of the 2D slice images,
   evaluating in each slice image if one or more 2D features are present along the panoramic curve, and
   combining the information of multiple slices to confirm the presence of a tooth.

2. The method according to claim 1, wherein the detecting is based on grey-scale value in the 3D model of the parts of the jaw.

3. The method according to claim 1 further comprising:
   (c) determining candidate implant dimensions, positions, orientations and configurations,
   (d) obtaining implant plans,
   (e) comparing implant plans to each other or to given criteria,
   (f) selecting or improving an implant plan.

4. The method according to claim 3, wherein step of determining candidate implant dimensions, positions, orientations and configurations comprises: defining point grids on respectively the incisal/occlusal and the apical sides of the restorative elements, connecting for each element, all points of the incisal/occlusal grid with all points of the apical grid, determining the intersection points of the obtained axes with the 3D model of the bone, placing implants from a digital implant library along the respective axes with the implant shoulders at a given distance from the entry point of the axes in the bone, listing all possible combinations going from a minimum of one set of alternatives for a single implant for the entire tooth setup to a maximum of all alternatives for an implant for each restorative element in the tooth setup.

5. The method according to claim 3, wherein in the step of determining candidate implant dimensions, positions, orientations and configurations an expert system is used to identify the type of implant case being treated and to suggest a typical corresponding implant plan based on the "best fit" of solutions in the expert system.

6. The method according to claim 3, wherein the step of obtaining implant plans comprises assigning scores to the implant combination(s) in function of measurements performed relative to the volume images of the patient or to the 3D models created in the step of creating 3D models of a tooth set up or of parts of the jaw.

7. The method according to claim 3, wherein in the step of obtaining implant plans comprises assigning scores to the implant combination(s) in function of the predicted loads on the implants using a biomechanical or finite element model of the jaw, implants and prosthesis.

8. The method according to claim 3, wherein the step of obtaining implant plans comprises assigning scores to the implant combination(s) in function of the achievable emergence profiles for individual implants.

9. The method according to claim 3, wherein the step of comparing implant plans to each other or to given criteria further comprises incrementally adjusting individual implant dimensions, positions and orientations in according with a predetermined strategy until the planning score reaches a given threshold value.

10. The method according to claim 1, wherein the step of generating 3D models of parts of the jaw comprises detecting image objects corresponding to natural or artificial teeth in the jaw.

11. The method according to claim 1, wherein in the step of generating a panoramic curve, the panoramic curve is calculated as the midline of the contour in the slice of the jaw.

12. The method according to claim 1, wherein the evaluating step includes calculating a correlation value between 2D matrices or features representing possible cross-sectional shapes of a tooth or tooth root and the grey-scales in local areas of the 2D slice images along the panoramic curve.

13. The method according to claim 1, wherein step of generating 3D models of parts of the jaw further comprises identifying zones of the jaw corresponding to the positions of individual teeth and attributing them the respective tooth numbers based on mean tooth width values and known dimensions of the jaw.

14. A non-transitory machine readable storage medium storing a computer program comprising instructions for carrying out the method recited in claim 1.

15. A system for preparing information for automated or semi-automated dental implant planning from image information relating to the jaw of a patient, comprising:
 (a) means for generating 3D models of parts of the jaw bone, and
 (b) means for detecting anatomical and artificial elements in the 3D model of the jaw bone and for automatically selecting zones in the jaw where implants can or cannot be placed based on image analysis, wherein the means for generating 3D models of parts of the jaw comprises:
 means for slicing the 3D model of the jaw into a number of 2D slice images, means for generating a panoramic curve for each of the 2D slice images,
 means for evaluating in each slice image if one or more 2D features are present along the panoramic curve, and
 means for combining the information of multiple slices to confirm the presence of a tooth.

* * * * *